(12) United States Patent
Menard

(10) Patent No.: US 7,088,233 B2
(45) Date of Patent: Aug. 8, 2006

(54) PERSONAL MEDICAL DEVICE COMMUNICATION SYSTEM AND METHOD

(75) Inventor: Raymond J. Menard, Hastings, MN (US)

(73) Assignee: Royal Thoughts, LLC, Minneapolis, MI (US)

( * ) Notice: Subject to any disclaimer, the term of this patent is extended or adjusted under 35 U.S.C. 154(b) by 0 days.

(21) Appl. No.: 10/165,624

(22) Filed: Jun. 7, 2002

(65) Prior Publication Data

US 2004/0027244 A9 Feb. 12, 2004

Related U.S. Application Data

(63) Continuation-in-part of application No. 09/956,474, filed on Sep. 19, 2001, which is a continuation of application No. 09/384,165, filed on Aug. 27, 1999, now Pat. No. 6,356,192, application No. 10/165,624, which is a continuation-in-part of application No. 10/112,669, filed on Mar. 28, 2002, and a continuation-in-part of application No. PCT/US01/18734, filed on Jun. 8, 2001.

(60) Provisional application No. 60/135,862, filed on May 25, 1999, provisional application No. 60/105,493, filed on Oct. 23, 1998, and provisional application No. 60/279,401, filed on Mar. 28, 2001.

(51) Int. Cl.
*G08B 1/08* (2006.01)

(52) U.S. Cl. .............................. 340/539.1; 340/539.11; 340/539.12; 340/539.13; 340/506; 340/531; 340/3.1; 340/533; 340/825.49

(58) Field of Classification Search .............. 340/539.1, 340/539.11, 539.12, 539.13, 506, 511, 517, 340/524, 533, 537, 3.1, 825.36, 825.49

See application file for complete search history.

(56) References Cited

U.S. PATENT DOCUMENTS

| 3,843,841 A | 10/1974 | Rubinstein |
| 3,969,709 A | 7/1976 | Isaacs et al. |
| 4,237,344 A | 12/1980 | Moore |

(Continued)

FOREIGN PATENT DOCUMENTS

| DE | 19962915 A1 | 9/2001 |
| WO | WO 01/26335 A3 | 4/2001 |
| WO | WO 01/47597 A2 | 7/2001 |

OTHER PUBLICATIONS

Bluetooth Product Design—a natural progression of our existing business,;RTX; 4 pgs.
Your Vision—Our Solution; RTX Telecom; 5 pgs.
Lucent Technologies and Bluetooth; Lucent Technologies, Inc.; Dec., 1999; 2 pgs.

(Continued)

*Primary Examiner*—Daryl Pope
(74) *Attorney, Agent, or Firm*—Gerald E. Helget; Briggs and Morgan, P.A.

(57) ABSTRACT

A personal and/or institutional health and wellness communications system, which may be used for a variety of emergency and non-emergency situations using two-way communication devices and a bi-directional communication network. In one application two-way pagers are adapted for use in the system. In one application cellular devices are adapted for use in the system. In one application an assisted living response center is established using various embodiments of the present personal and/or institutional communications system. The system provides multiple levels of prioritization, authentication of person (task, step, process or order), and confirmation via interrogation of person, device, or related monitor. One embodiment provides a method for receiving, evaluating and responding to calls received from a subscriber, patient, related party, or health care provider or health care system.

57 Claims, 9 Drawing Sheets

U.S. PATENT DOCUMENTS

| | | |
|---|---|---|
| 4,284,849 A | 8/1981 | Anderson et al. |
| 4,303,801 A | 12/1981 | Anderson et al. |
| 4,531,527 A | 7/1985 | Reinhold, Jr. . |
| 4,772,876 A | 9/1988 | Laud |
| 4,843,377 A | 6/1989 | Fuller et al. |
| 4,856,047 A | 8/1989 | Saunders |
| 4,908,600 A | 3/1990 | Martinez |
| 4,993,059 A | 2/1991 | Smith et al. |
| 4,994,787 A | 2/1991 | Kratt et al. |
| 5,016,172 A | 5/1991 | Dessertine |
| 5,025,374 A | 6/1991 | Roizen et al. |
| 5,062,147 A | 10/1991 | Pickett |
| 5,081,667 A | 1/1992 | Drori et al. |
| 5,128,979 A | 7/1992 | Reich et al. |
| 5,179,571 A | 1/1993 | Schilling |
| 5,195,126 A | 3/1993 | Carrier et al. |
| 5,223,844 A | 6/1993 | Mansell et al. |
| 5,228,449 A | 7/1993 | Christ et al. |
| 5,276,728 A | 1/1994 | Pagliaroli et al. |
| 5,278,539 A | 1/1994 | Lauterbach et al. |
| 5,319,355 A | 6/1994 | Russek et al. |
| 5,319,698 A | 6/1994 | Glidewell |
| 5,333,173 A | 7/1994 | Seazholtz et al. |
| 5,351,235 A | 9/1994 | Lahtinen |
| 5,390,238 A | 2/1995 | Kirk et al. |
| 5,398,782 A | 3/1995 | Talbot |
| 5,402,466 A | 3/1995 | Delahanty |
| 5,404,577 A | 4/1995 | Zuckerman et al. |
| 5,412,372 A | 5/1995 | Parkhurst et al. |
| 5,416,695 A | 5/1995 | Stutman et al. |
| 5,432,841 A | 7/1995 | Rimer |
| 5,451,839 A | 9/1995 | Rappaport et al. |
| 5,485,504 A | 1/1996 | Ohnsorge |
| 5,513,111 A | 4/1996 | Wortham |
| 5,568,535 A | 10/1996 | Sheffer et al. |
| 5,570,083 A | 10/1996 | Johnson |
| 5,583,831 A | 12/1996 | Churchill et al. |
| 5,587,701 A | 12/1996 | Hess |
| 5,630,207 A | 5/1997 | Gitlin et al. |
| 5,640,147 A | 6/1997 | Chek et al. |
| 5,652,564 A | 7/1997 | Winbush |
| 5,652,570 A | 7/1997 | Lepkofker |
| 5,687,215 A | 11/1997 | Timm et al. |
| 5,712,619 A | 1/1998 | Simkin |
| 5,719,551 A | 2/1998 | Flick |
| 5,736,932 A | 4/1998 | Bulfer et al. |
| 5,739,748 A | 4/1998 | Flick |
| 5,742,233 A | 4/1998 | Hoffman et al. |
| 5,752,976 A | 5/1998 | Duffin et al. |
| 5,754,111 A | 5/1998 | Garcia |
| 5,777,551 A | 7/1998 | Hess |
| 5,784,685 A | 7/1998 | Stanford et al. |
| 5,786,746 A | 7/1998 | Lombardo et al. |
| 5,793,283 A | 8/1998 | Davis |
| 5,812,536 A | 9/1998 | Manduely |
| 5,815,417 A | 9/1998 | Orr et al. |
| 5,821,854 A | 10/1998 | Dorinski et al. |
| 5,825,283 A | 10/1998 | Camhi |
| 5,845,203 A | 12/1998 | LaDue |
| 5,850,180 A | 12/1998 | Hess |
| 5,850,344 A | 12/1998 | Conkright |
| 5,852,408 A | 12/1998 | Christiansen et al. |
| 5,870,020 A | 2/1999 | Harrison, Jr. |
| 5,873,043 A | 2/1999 | Comer |
| 5,874,889 A | 2/1999 | Higdon et al. |
| 5,892,442 A | 4/1999 | Ozery |
| 5,894,591 A | 4/1999 | Tamayo |
| 5,898,391 A | 4/1999 | Jefferies et al. |
| 5,898,904 A | 4/1999 | Wang |
| 5,902,234 A | 5/1999 | Webb |
| 5,907,279 A | 5/1999 | Bruins et al. |
| 5,917,405 A | 6/1999 | Joao |
| 5,933,080 A | 8/1999 | Nojima |
| 5,959,529 A | 9/1999 | Kail, IV |
| 6,023,223 A | 2/2000 | Baxter, Jr. |
| 6,023,241 A | 2/2000 | Clapper |
| 6,028,514 A | 2/2000 | Lemelson et al. |
| 6,035,021 A | 3/2000 | Katz |
| 6,044,257 A | 3/2000 | Boling et al. |
| 6,057,758 A | 5/2000 | Dempsey et al. |
| 6,087,952 A | 7/2000 | Prabhakaran |
| 6,118,866 A | 9/2000 | Shtivelman |
| 6,288,641 B1 | 9/2001 | Casais |
| 6,295,346 B1 | 9/2001 | Markowitz et al. |
| 6,340,928 B1 | 1/2002 | McCurdy |
| 6,388,612 B1 | 5/2002 | Neher |

OTHER PUBLICATIONS

Houston, Jerry; Socket Teams with Cambridge Silicon Radio for Bluetooth Cordless Networking on Windows CE; Socket Communications, Inc., 1999; 2 pgs.

Technology Solutions for Bluetooth; Ericsson Microelectronics; Nov., 1999; 2 pgs.

The Secret of Success!, Signal Newletter No. 3—The Official Newsletter of the Bluetooth Special Interest Group; Nov., 1999; 8 pgs.

Unleash the World—Core Technology for Bluetooth applications; Ericsson Mobile Communications AB, 1999; 7 pgs.

Wireless Connections Made Easy; Bluetooth; 19 pgs.

Get a better vantage point and outmaneuver the competition; Cadence Design Systems, Inc.; 1999; 2 pgs.

Empowering the mobile enterprise; Puma Technology, Inc.; 1996–1999; 2 pgs.

Designing Solutions for the Internet Economy, Intel Developer Forum Spring 2000; Feb. 15–17, 2000; 2 pgs.

Socket's Bluetooth Cordless Communications Card; Socket Communications, Inc.; Dec., 1999; 2 pgs.

Nobel, Carmen; Microsoft jumps on Bluetooth bandwagon; PC Week; Dec. 6, 1999; 1 pg.

CreataLink; Motorola, Inc., 1999; 2 pgs.

Bluetooth White Paper; AU–System AB; 1999; entire pamphlet.

Object GEODE—The Most Advanced Integrated Environment for the Development of Distributed Real–time Systems; VERIOLOG S.A.; 1998; entire brochure.

Bluetooth—solutions for personal area networking; TDK Systems, Inc.; 4 pgs.

Digianswer Bluetooth—Development and Demonstration Tools Product Sheet; DIGIANSWER A/S; 6 pgs.

The Ericsson Bluetooth Development Kit, Ericsson Mobile Communications, AB; 1999; 2 pgs.

Bluetooth Blue–Share Product Brief; ACER NeWeb Corporation; 1 pg.

Blue–Connect Product Brief; ACER NeWeb Corporation; 1 pg.

Bluetooth Development using SDL, MSC and TTCN; Telelogic AB; 13 pgs.

Emlation System Speeds Development of CDMA Satcom Handsets; Penton Publishing, Inc.; 1997; 4 pgs.

DIGIANSWER/Bluetooth Technology; Digainswer (lrl) Ltd.; 8 pgs.

UMTS W–CDMA Technology Development Using the Aptix System Explorer MP4 for Algorithm Verification; Aptix Corporation; 1999; 4 pgs.

ARM9 Thumb Family; Arm Ltd.; 6 pgs.

Enabling Innovation; Arm Ltd.; 1999; 10 pgs.

Arm7 Thumb Family; Arm Powered; 4 pgs.

IVT—Bluetooth Protocol Stack SDL/C Source Code; Bluetooth; 2 pgs.

Spontaneous Connections; CommVerge; May, 2000; 6 pgs.

OSE—the new generation realtime operating system; ENA OSE Systems; 1999; entire booklet.

Alarmnet–M Mobitex System; ArlamNet; 2000; 1 pg/.

AlarmNet–C Control Channel Cellular; AlarmNet; 2000; 2 pgs.

Samsung Electronics Joins Home Radio Frequency Group in Development of Wireless Network for the Home; Samsung Electronics, 1998; pp. 1–2.

Tachless Remote Engine Starters; ALMEX, 2000; pp. 1–3.

Introduction to the HomeRF Technical Specification; HomeRF; 2000; pp. 1–17.

Posti, J.; Motorola Introduces CreataLink 2 XT two–way data transceiver; Motorola Press Release; Mar., 1999; 2 pgs.

CreataLink 2XT; Motorola Messaging Products; Mar., 1999; 1 pg.

CreataLink 2XT; Motorola; Nov., 2000; 1 pg.

Skyroute Wireless Communications; 1974; pp. 1–4.

21$^{st}$ Century Emergency Safety Communications Policy; ComCARE Alliance; 2000; pp. 1–3.

AllNetDevices:—Geoworks, Openwave End Patent Fight; allNetDevices; 2000; 1 pg.

Automatic Crash Notification, ComCARE Alliance; 2000; 2 pgs.

Connect 24 Data Communications; Connect 24; 2001; 1 pg.

Emergency 911 Cellular Phone and Cellular Phone Accessories; AAA Communications; 2001; 7 pgs.

Glossary; ComCARE Alliance; 2000; 3 pgs.

PSAP Updates and Third–Party Call Centers; ComCARE Alliance; 2000; 2 pgs.

Will the push—not pull—of Internet information dramatically alter our Web interactions?; Sunworld; 2000; 6 pgs.

ORA Electronics Introduces Rescue Mate, a Complete Cellular Telephone Safety Package; Hands–Free Operation, Instant Emergency 911 Access, Roadside Assistance Services; Business Wire; 1998; 2 pgs.

AllNetDevices:—The Device–Centric Home in 2000: Close, But No Cigar; Dec. 26, 2000; 3 pgs.

AlarmNet–A Original AlarmNet; Dec. 27, 2000; 2 pgs.

Bluetooth; Wireless Connections Made Easy; 20 pgs.

PERSONAL MEDICAL DEVICE COMMUNICATION SYSTEM AND METHOD

The present application is a continuation-in-part of U.S. patent application Ser. No. 09/956,474 filed Sep. 19, 2001, which is a continuation of U.S. patent application Ser. No. 09/384,165, filed Aug. 27, 1999 and now issued as U.S. Pat. No. 6,356,192, which claims priority to U.S. provisional patent application Ser. No. 60/135,862, filed May 25, 1999 and to U.S. provisional patent application Ser. No. 60/105,493 filed Oct. 23, 1998. The present application is also a continuation-in-part of co-pending U.S. patent application Ser. No. 10/112,669, filed Mar. 28, 2002, which claims priority to a provisional patent application Ser. No. 60/279,401, filed Mar. 28, 2001. The present application is also a continuation-in-part and claims the benefit of International Application No. PCT/US01/18734, filed Jun. 8, 2001.

BACKGROUND OF THE INVENTION

The present invention relates generally to bi-directional personal and health-wellness provider communication system and in particular to a personal communication system suitable for use with children, vulnerable adults (such as those in assisted living situations), and more specifically, medically distressed persons and those in whom an personal medical device has been deployed, for medical testing, and for other life enhancements.

There are several trends which taken together are causing a change in the way medical services are delivered. Among other things, these include longer lifespan, medical technology improvements, automation of diagnostic processes, specialization of caregivers, the rapid pace of technology that causes a shortening of the amortization of development and investment costs, increasing expense of medical care centers, and the shortage of health care workers.

The results of these trends are manifold. They include moving more of the delivery of services out of a medical center and away from the direct supervision of highly trained medical personnel. They include providing personal medical devices to allow long-term patients to resume a more mobile lifestyle. They include allowing patients to be treated from home for issues of cost and comfort. They include reducing the level of training associated with caregivers so that in some cases, even a casual passerby is able to provide meaningful assistance with devices once associated only with properly trained medical personnel, for example using Portable Automated Defibrillators. However, the remoteness of patients from professional caregivers increases the need for communications systems to monitor the patient, deliver care, and communicate.

What is needed in the art is an improved detection system that is friendly to a mobile user, that is easy to adapt to existing devices, that is easy to install, that is inexpensive, and that provides substantial interoperability between wireless technologies, communication network providers, and other widely used medical and public systems.

SUMMARY OF THE INVENTION

One skilled in the art will readily recognize that the embodiments described solve all of these problems and many more not mentioned expressly herein.

Personal Medical Devices (PMD) take many forms. PMDs may be surgically implanted, strapped externally to the body, carried in a pocket, transported in a carrying case, or installed as a home appliance. They may be used only for rare emergencies, on an occasional basis, on a regular schedule, or in a continuous or nearly continuous fashion. PMDs may monitor individual or combinations of body functions such as heart function, respiration, body chemistry, brain function, or muscular/skeleton actions. PMDs may provide body functions such as mechanical hearts, kidney dialysis, digestive or respiratory activities. PMDs may be used to deliver drugs, heart defibrillation, or other treatment. PMDs may be used to enhance wellness, test drug therapies, monitor patient health, deliver long-term care, or treat acute conditions.

We describe a device and method to couple with PMDs to provide wireless communication and locating functions. The purpose for communications include but are not limited to the following: to provide health care professionals with access to information for remote diagnostic capabilities; to provide notification of acute conditions possibly requiring immediate assistance, transportation to a medical center, or remote treatment action; to provide a location information of mobile persons for caregivers; to notify responsible parties of the occurrence of a medical condition; and to provide remote intervention assistance by caregivers through verbal or visual interaction.

In one embodiment, in order to provide mobility for users of PMDs in a public environment, we employ standard network communication systems to deliver a comprehensive medical communications service. In one embodiment, the communications network links together the PMD, casual caregivers, a medical center, an emergency dispatch center, medical databases, and related responsible parties. This group of associated parties is able to combine resources to improve the survivability during an acute medical event.

In one embodiment, the medical communications system delivers an end-to-end comprehensive solution to provide care to a remote or mobile user of a PMD.

DETAILED DESCRIPTION OF THE PREFERRED EMBODIMENTS

This detailed description provides a number of different embodiments of the present system. The embodiments provided herein are not intended in an exclusive or limited sense, and variations may exist in organization, dimension, hardware, software, mechanical design and configuration without departing from the claimed invention, the scope of which is provided by the attached claims and equivalents thereof.

The present system provides many benefits, including but not limited to, low cost, easy installation, limited power requirements and wireless operation and signal transmission. Many other benefits will be appreciated by those skilled in the art upon reading and understanding the present description.

U.S. Provisional Patent Application No. 60/098,392, filed Aug. 29, 1998; U.S. Provisional Patent Application No. 60/098,270 filed Aug. 28, 1998; U.S. Provisional Patent Application No. 60/105,493 filed Oct. 23, 1998; and U.S. Provisional Patent Application No. 60/135,862 filed May, 25, 1999, are all hereby incorporated by reference in their entirety.

Personal Medical Device

Figure 1:
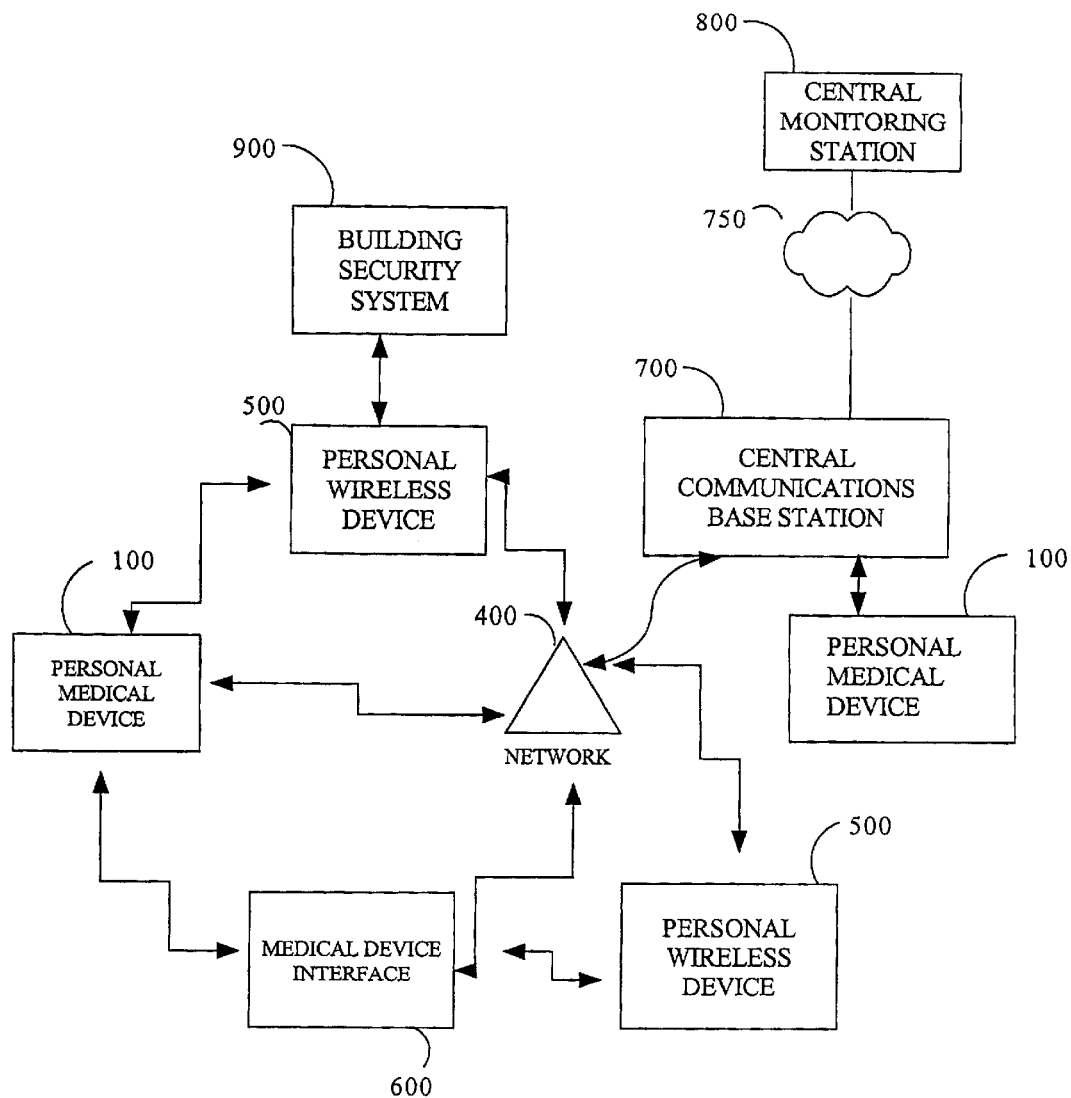
FIG. 1 is a block diagram showing the overall structure of the system of the present invention.

FIG. 1 is a block diagram showing the interoperability of a personal medical device (PMD) 100 with a medical device interface (MDI) 200 and a network 400. As can be seen, the PMD 100 may interact directly with the network 400 or through the mediation of the MDI 200. Alternatively, the PMD may interact with a personal wireless device 500 which in turn interacts with the network.

Figure 2:
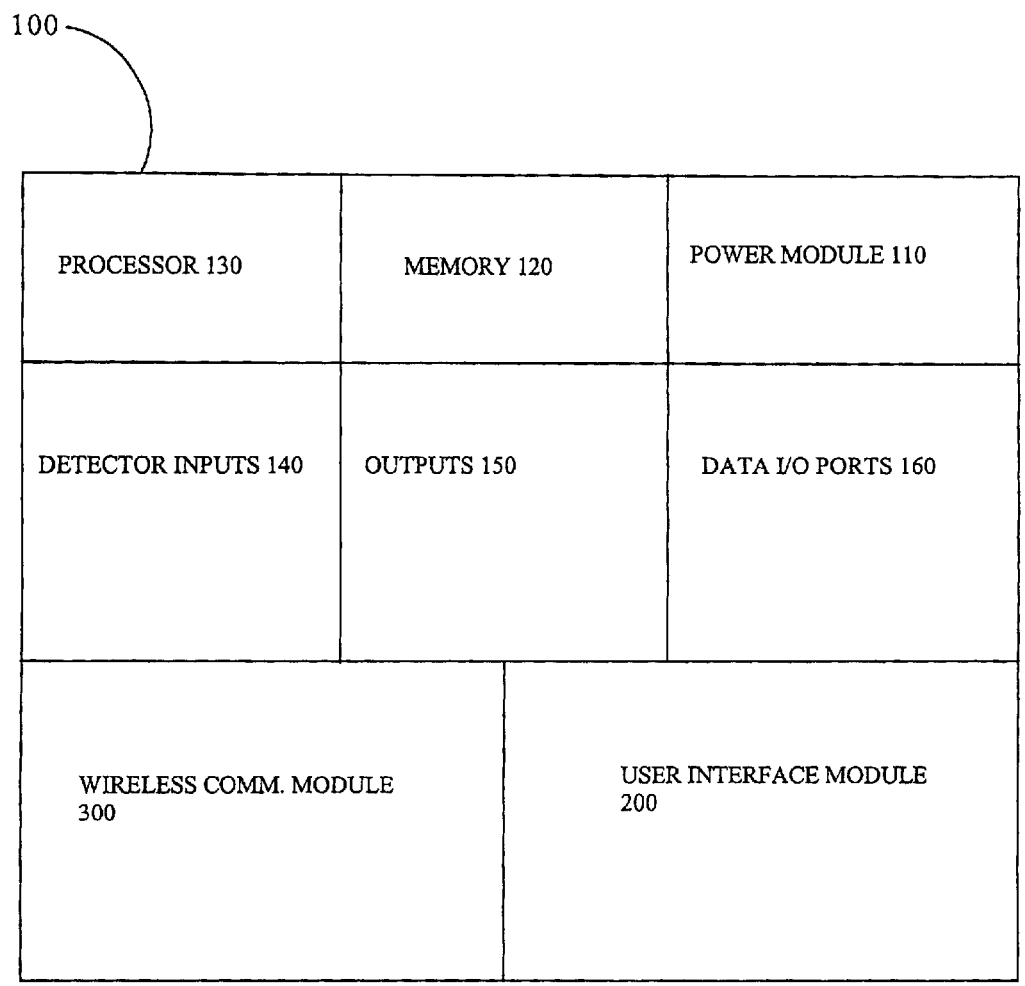
FIG. 2 is a block diagram showing the internal structure of a portable device.

FIG. 2 is a block diagram depicting the components of one embodiment of a PMD 100. In one embodiment, the PMD includes a power module 110. The power module 110 may be a battery or a line connection. If a battery, it may be rechargeable. In one embodiment the PMD includes a memory 120. In one embodiment the PMD includes a processor 130. The processor 130 executes instructions from its programming and also may participate in data transfer between other components of the PMD 100.

Optionally, PMD 100 has connections to related external or embedded devices. In one embodiment, PMD 100 includes connections to detectors 140. Detectors 140 may be any sensor of bodily or physiological parameters such as, but not limited to: temperature, motion, respiration, blood oxygen content, electrocardiogram (ECG), electroencephalogram (EEG), and other measurements.

Optionally, PMD 100 has connections to outputs 150. The outputs may be signaled by changes in voltages, impedance, current, magnetic field, electromagnetic energy such as radio frequency signals, infrared signals or optical signals, and audible or other forms of mechanical energy. The outputs may be direct changes of state, analog, or digital in form. Several embodiments are possible, and the examples given herein are not intended in a limiting or restrictive sense. The outputs may be activated and controlled by the medical device interface 200 or the processor 130, or by the actuation of the detector 140 or a combination of these. The outputs 150 may be used, for example, to actuate solenoids, operate motors, or apply electrical current to the heart.

Optionally, PMD 100 has connections to data input/output ports 160. Data I/O ports 160 may include, but are not limited to: serial, parallel, USB, etc.

Optionally, PMD 100 includes a User Interface Module (UIM) 200. The UIM 200 may allow users to view or enter data, conduct voice communications, use a camera to transmit images, or view a screen for graphical images.

Optionally, PMD 100 includes a wireless communications module 300. In one embodiment the wireless communications module includes systems and standards for Local Area Wireless 330. In one embodiment the wireless communications are designed to be Network Based Communications (NBC) 360.

User Interface

Figure 3:
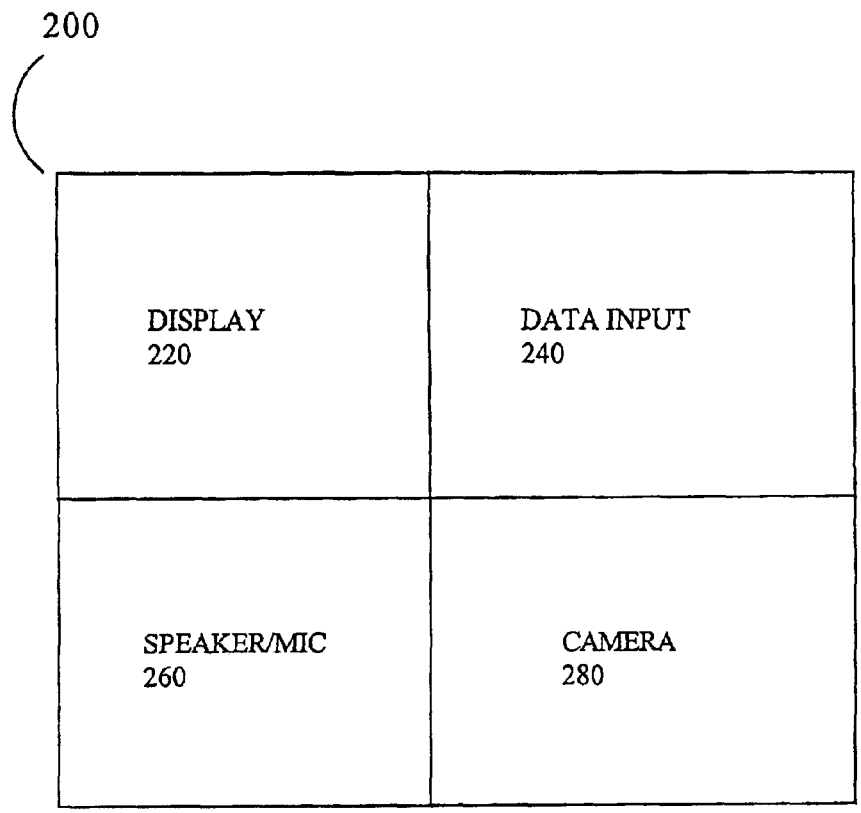
FIG. 3 is a block diagram showing the structure of a user interface module.

FIG. 3 depicts User Interface Module (UIM) 200. In one embodiment of UIM 200, display 220 is included. Display 220 may be any standard device for displaying information, such as a CRT, plasma display, LED, LCD, etc. or equivalent.

Preferably the UIM 200 includes data input means 240. Data input means may be any standard means for inputting information, such as a keypad, touch screen, bar code scanner, telephone keypad, buttons, switches, etc., or equivalent.

In one embodiment of UIM 200, a speaker/microphone module 260 is included. Speaker/microphone module may be any device for producing sound, such as a speaker or microphone or the equivalent.

In one embodiment of UIM 200, a camera 280 is included. Camera 280 may be a still camera, video camera, etc.

Communications

FIGS. 4A–4E depict various possible wireless communication paths that may be used by the PMD 100 to connect to the long-range bi-directional network 400.

Figure 4A:
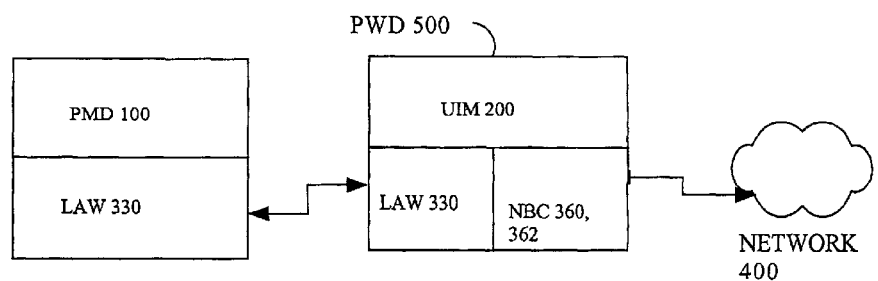
FIGS. 4A–4F are block diagrams showing various configurations of the system of the present invention.

FIG. 4A depicts one embodiment of the present system. PMD 100 communicates to Personal Wireless Device (PWD) 500 with local area wireless (LAW) 330. PWD 500 includes a LAW 330 compatible with LAW 330 in PMD 100. In one embodiment, PWD 500 includes a UIM 200. PWD 500 includes network based communications (NBC) 360. NBC 360 communicates information received from LAW 330 to long-range bi-directional network 400.

Figure 4B:
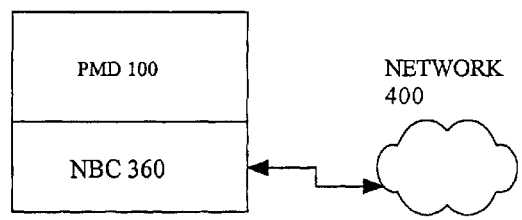

FIG. 4B depicts another embodiment of the present system. PMD 100 communicates to the network 400 through NBC 360. LAW 330 is not employed.

Figure 4C:
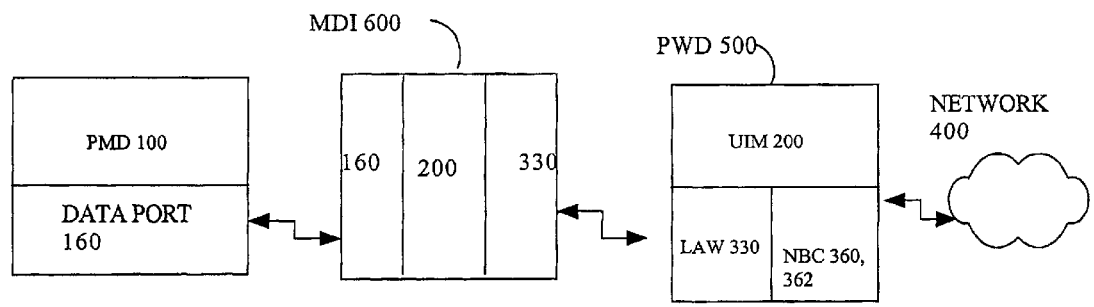

FIG. 4C depicts another embodiment of the present system. PMD 100 communicates through data port 160 to Medical Device Interface (MDI) 600. In one embodiment, MDI 600 includes a UIM 200. In this embodiment, MDI 600 includes a LAW 330 and communicates to PWD 500 through LAW 330. PWD 500 includes a LAW 330 compatible with MDI 600. Preferably, PWD 500 includes UIM 200. Preferably, PWD 500 includes NBC 360 and communicates to long-range bi-directional 400 through NBC 360.

Figure 4D:
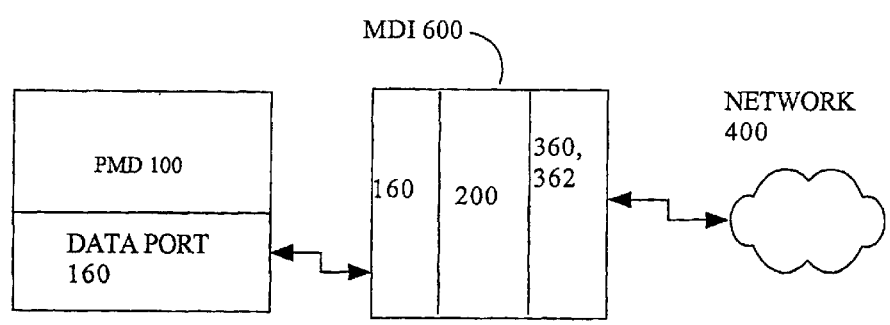

FIG. 4D depicts another embodiment of the present system. PMD 100 communicates through data port 160 to MDI 600. MDI 600 may include UIM 200. Preferably, MDI 600 includes NBC 360 and communicates to long-range bi-directional network 400 through NBC 360.

Figure 4E:
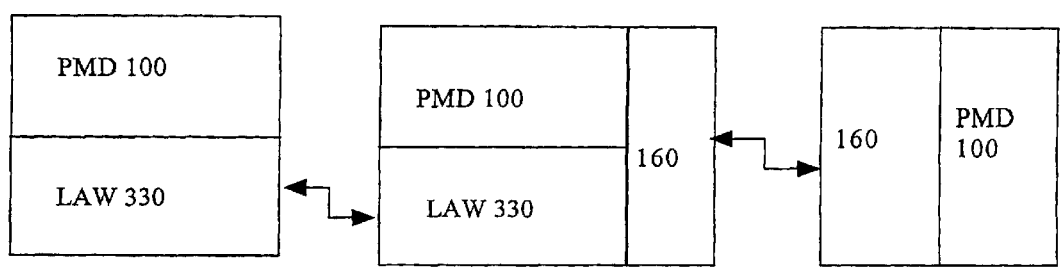

FIG. 4E depicts another embodiment of the present system. PMD 100 communicates through LAW 330 to another PMD 100, which in turn communicates through data port 160 to a third PMD 100.

Figure 4F:
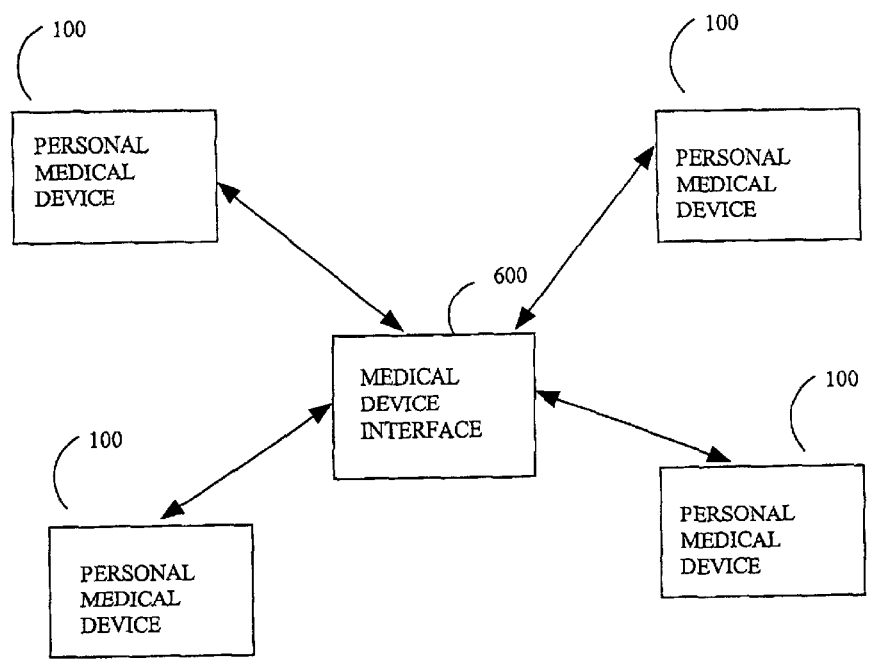

FIG. 4F shows that a single medical device interface 600 can communicate simultaneously with multiple PMDs 100.

About Local Area Wireless Communications

LAW 330 may include, but is not limited to, infrared or radio frequency (RF). Any suitable RF system that conforms to FCC requirements and power requirements may be used. Preferably, the BLUETOOTH standard is used. BLUETOOTH is a 2.4 GHz wireless technology employed to transport data between cellular phones, notebook PCs, and other handheld or portable electronic gear at speeds of up to 1 megabit per second. The BLUETOOTH standard was developed by the Bluetooth Special Interest Group ("BSIG"), a consortioum formed by Ericsson, IBM, Intel, Nokia, and Toshiba. The BLUETOOTH standard is designed to be broadband compatible and capable of simultaneously supporting multiple information sets and architecture, transmitting data at relatively high speeds, and providing data, sound, and video services on demand. Of course, other suitable wireless communication standards and methods now existing or developed in the future are contemplated in the present invention. In addition, embodiments are contemplated that operate in conjunction with a BLUETOOTH or BLUETOOTH-like wireless communication standard, protocol, or system where a frequency other than 2.4 GHz is employed, or where infrared, optical, or other communication means are employed in conjunction with BLUETOOTH or BLUETOOTH-like wireless RF communication techniques.

In one embodiment, the present system includes a transceiver in compliance with BLUETOOTH® technical specification version 1.0, herein incorporated by reference. In one embodiment, the present system includes a transceiver in compliance with standards established, or anticipated to be established, by the Bluetooth Special Interest Group.

In one embodiment, the present system includes a transceiver in compliance with standards established, or anticipated to be established, by the Institute of Electrical and Electronics Engineers, Inc., (IEEE). The IEEE 802.15 WPAN standard is anticipated to include the technology developed by the BLUETOOTH® Special Interest Group. WPAN refers to Wireless Personal Area Networks. The IEEE 802.15 WPAN standard is expected to define a standard for wireless communications within a personal operating space (POS) which encircles a person.

In one embodiment, the transceiver is a wireless, bi-directional, transceiver suitable for short-range, omnidirectional communication that allows ad hoc networking of multiple transceivers for purposes of extending the effective range of communication. Ad hoc networking refers to the ability of one transceiver to automatically detect and establish a digital communication link with another transceiver. The resulting network, known as a piconet, enables each transceiver to exchange digital data with the other transceiver. According to one embodiment, BLUETOOTH® involves a wireless transceiver transmitting a digital signal and periodically monitoring a radio frequency for an incoming digital message encoded in a network protocol. The transceiver communicates digital data in the network protocol upon receiving an incoming digital message.

According to one definition, and subject to the vagaries of radio design and environmental factors, short-range may refer to systems designed primarily for use in and around a premises and thus, the range generally is below a mile. Short-range communications may also be construed as point-to-point communications, examples of which include those compatible with protocols such as BLUETOOTH®, HomeRF™, and the IEEE 802.11 WAN standard (described subsequently). Long-range, thus, may be construed as networked communications with a range in excess of short-range communications. Examples of long-range communication may include, Aeris MicroBurst cellular communication system, and various networked pager, cellular telephone or, in some cases, radio frequency communication systems.

In the event that transceiver includes a transceiver compatible with BLUETOOTH® protocol, for example, then the personal device may have sufficient range to conduct bidirectional communications over relatively short-range distances, such as approximately 10 to 1,000 meters or more. In some applications, this distance allows communications throughout a premise.

LAW 330 may include a separate, integrated or software based short-range bi-directional wireless module. The short-range network may be based upon HomeRF, 802.11, Bluetooth or other conventional or unconventional protocols. However, these are short-range networks and the meaning imposed herein is to include premises and facility based wireless networks and not to describe long-range networks such as cellular telephone networks used to communicate over long-distances. Such a system may include programmable or automatically selecting electronics to decide whether to conduct communications between the network module and an optional base station using the short-range module or the network module. In one embodiment the system may employ different portions of the network to provide short-range or long-range network connections, depending on the distance between the devices and the base stations. In one such embodiment, the network automatically adjusts for different required transmission distances.

In one embodiment, the transceiver is compatible with both a long-range communication protocol and a short-range communication protocol. For example, a person located a long distance away, such as several miles, may communicate with the transceiver using a cellular telephone compatible with the long-range protocol of transceiver.

Other short-range communication protocols are also contemplated and the foregoing examples are not to be construed as limitations but merely as examples.

About Long-Range Bi-Directional Network Based Communications

Long-range network based communications 360 refers to a type of communications system that has a greater range than LAW 330, primarily because more power is available and/or because of an FCC license.

NBC 360 may include a long-range wireless communications network 362, such as a cellular network, satellite network, paging network, narrowband PCS, narrowband trunk radio, or other wireless communication network. Combinations of such networks and other embodiments may be substituted without departing from the present system.

In one embodiment, the long-range wireless network 362 is a cellular communications network. In another embodiment, the long-range wireless network is a paging network. In another embodiment the long-range wireless network is a satellite network. In another embodiment the long-range wireless network is a wideband or narrowband PCS network. In another embodiment the long-range wireless network is a wideband or narrowband trunk radio module. Other networks are possible without departing from the present system. In one embodiment, the NBC 360 supports multiple network systems, such as a cellular module and a two-way paging module, for example. In such embodiments, the system may prefer one form of network communications over another and may switch depending on a variety of factors such as available service, signal strength, or types of communications being supported. For example, the cellular network may be used as a default and the paging network may take over once cellular service is either weak or otherwise unavailable. Other permutations are possible without departing from the present system.

The long-range wireless network 362 employed may be any consumer or proprietary network designed to serve users in range of the detection system, including, but not limited to, a cellular network such as analog or digital cellular systems employing such protocols and designs as CDPD, CDMA, GSM, PDC, PHS, TDMA, FLEX™, ReFLEX™, iDEN™, TETRA™, DECT, DataTAC™, and Mobitex™, RAMNET™ or Ardis™ or other protocols such as trunk radio, Microburst™, Cellemetry™, satellite, or other analogue or digital wireless networks or the control channels or portions of various networks. The networks may be proprietary or public, special purpose or broadly capable. However, these are long-range networks and the meaning imposed herein is not to describe a premises or facility based type of wireless network.

The long-range wireless network 362 may employ various messaging protocols. In one embodiment Wireless Application Protocol (WAP) is employed as a messaging protocol over the network. WAP is a protocol created by an international body representing numerous wireless and computing industry companies. WAP is designed to work with most wireless networks such as CDPD, CDMA, GSM, PDC, PHS, TDMA, FLEX, ReFLEX, iDEN, TETRA, DECT, DataTAC, and Mobitex and also to work with some Internet protocols such as HTTP and IP. Other messaging protocols such as iMode™, WML, SMS and other conventional and unconventional protocols may be employed without departing from the design of the present embodiment.

As an example, these long-range communication protocols described above may include, but are not limited to, cellular telephone protocols, one-way or two-way pager protocols, and PCS protocols. Typically, PCS systems operate in the 1900 MHZ frequency range. One example, known as Code-Division Multiple Access (CDMA, Qualcomm Inc., one variant is IS-95) uses spread spectrum techniques. CDMA uses the full available spectrum and individual messages are encoded with a pseudo-random digital sequence. Another example, Global Systems for Mobile communications (GSM), is one of the leading digital cellular systems and allows eight simultaneous calls on the same radio frequency. Another example, Time Division Multiple Access (TDMA, one variant known as IS-136) uses time-division multiplexing (TDM) in which a radio frequency is time divided and slots are allocated to multiple calls. TDMA is used by the GSM digital cellular system. Another example, 3G, promulgated by the ITU (International Telecommunication Union, Geneva, Switzerland) represents a third generation of mobile communications technology with analog and digital PCS representing first and second generations. 3G is operative over wireless air interfaces such as GSM, TDMA, and CDMA. The EDGE (Enhanced Data rates for Global Evolution) air interface has been developed to meet the bandwidth needs of 3G. Another example, Aloha, enables satellite and terrestrial radio transmissions. Another example, Short Message Service (SMS), allows communications of short messages with a cellular telephone, fax machine and an IP address. Messages are limited to a length of 160 alpha-numeric characters. Another example, General Packet Radio Service (GPRS) is another standard used for wireless communications and operates at transmission speeds far greater than GSM. GPRS can be used for communicating either small bursts of data, such as e-mail and Web browsing, or large volumes of data.

In one embodiment, a long-range communication protocol is based on two way pager technology. Examples of two way pager protocols include ReFLEX™ (Motorola) format, InFLEXion© (Motorola) format, NexNet© (nexus Telecommunications Ltd. of Israel) format and others.

Other long-range communication protocols are also contemplated and the foregoing examples are not to be construed as limitations but merely as examples.

About the Personal Wireless Device and Medical Device Interface

A medical device interface 600 is similar to a personal wireless device 500 except that network based communications 360 is opt ional with a medical device interface 600.

The personal wireless device 500 or medical device interface 600 may be of several different designs. For example, in one embodiment it may be a "response messaging" capable two-way pager. This is service where a two-way pager receives a message and optional multiple-choice responses. The user can select the appropriate responses. Such a design may be adapted to provide basic control options related to the system.

In another embodiment, the personal wireless device 500 or medical device interface 600 may be a programmable two-way paging device such as the Motorola PageWriter™ 2000. This is a class of device that acts as both a two-way pager and a handheld computer also known as a PDA (Personal Digital Assistant).

In another embodiment, the personal wireless device 500 or medical device interface 600 may be a cellular telephone. The cell phone may be analog or digital in any of the various technologies employed by the cell phone industry such as PCS, or CDMA, or TDMA, or others. The cell phone may have programmable capability such as is found in a Nokia™ 9000 series of devices.

In embodiments where the user employs standard or adapted paging or cell phones as their personal wireless device 500 or medical device interface 600, security passwords may be entered by using numeric or other keys on a phone. In another embodiment, the security password may be entered by speaking words. In this embodiment, the system may use word recognition, voice recognition or a combination of these technologies. In the embodiment of a pager, a distinct order of pressing certain keys could provide the equivalent of a security code. For example, 3 short and 1 long on a certain key; or once on key 'a', once on key 'b', and once more on key 'a'.

In another embodiment, the personal wireless device 500 or medical device interface 600 is a handheld computer. Many personal digital assistants (PDAs) offer programmable capability and connectivity to various types of long-range wireless networks. An example of this type of device is the PalmPilot™ or Palm series of devices manufactured by Palm, Inc. In these embodiments where a programmable personal wireless device 500 or medical device interface 600 is used such as a PalmPilot, PageWriter or programmable cell phone, the programmable nature of the devices facilitates the implementation of industry-standard designs and would allow for the development of a program written for the devices.

In another embodiment, a special manufactured device may be manufactured to serve the needs of the system user.

In another embodiment, the personal medical device 100 is directly connected to a personal wireless device 500 that is manufactured as an integrated unit.

About the Central Communications Base Station

In one embodiment, the personal medical device 100 communicates with a device referred to herein as central communication base station 700. Central communication base station 700 may include a first transceiver compatible with BLUETOOTH® or other short-range wireless network as described herein. Base station may provide a repeater service to receive a message using BLUETOOTH® and to retransmit the message using a different communication protocol or also using BLUETOOTH® communication protocol.

Base station 700 may also include a second transceiver or a wired interface having access to another communication network 750. The second transceiver or wired interface may retransmit the signal received from the personal device 100 or received from some other device. In this way, central communication base station 700 may serve to extend the communication range of the personal device. For example, a message between the personal device and an emergency-dispatch center may be coupled to communication with the base station 700 connected network 750 and a short-range wireless network. Communications between the personal device 100 and a device coupled to communicate with the base station 700 connected network 750 may be considered long-range communications.

Base station may 700 also communicate bi-directionally within the premise with one or more additional compatible devices. These may be a second personal device 100 or any other device.

The base station connected network 750 may be a public switched telephone network (PSTN), a pager communication network, a cellular communication network, a radio communication network, the Internet, or some other communication network. It will be further appreciated that with a suitable repeater, gateway, switch, router, bridge or network interface, the effective range of communication of a short-range transceiver may be extended to any distance. For example, base station 700 may receive transmissions on a BLUETOOTH® communication protocol and provide an interface to connect with the base station connected network 750, such as the public switched telephone network (PSTN) using the base station link. In this case, a wired telephone at a remote location can be used to communicate with the personal device 100. As another example, the range may be extended by coupling a BLUETOOTH® transceiver with a cellular telephone network, a narrow band personal communication systems ("PCS") network, a CELLEMETRY® network, a narrow band trunk radio network or other type of wired or wireless communication network.

Examples of devices compatible with such long-range protocols include, but are not limited to, a telephone coupled to the public switched telephone network (PSTN), a cellular telephone, a pager (either one way or two way), a personal communication device (such as a personal digital assistant, PDA), a computer, or other wired or wireless communication device.

In one embodiment, the long distance network 750 may include a telephone network, which may include an intranet or the Internet. Coupling to such a network may be accomplished, for example, using a variety of connections, including a leased line connection, such as a T-1, an ISDN, a DSL line, or other high-speed broadband connection, or it may entail a dial-up connection using a modem. In one embodiment, the long distance network 750 may include a radio frequency or satellite communication network. In addition, one or more of the aforementioned networks may be combined to achieve desired results.

Short-range communication protocols, compatible with the base station may include, but are not limited to, wireless protocols such as HomeRF™, BLUETOOTH®, wireless LAN (WLAN), or other personal wireless networking technology. HomeRF™, currently defined by specification 2.1, provides support for broadband wireless digital communications at a frequency of approximately 2.45 GHz.

Other long-range and short-range communication protocols are also contemplated and the foregoing examples are not to be construed as limitations but merely as examples.

The base station 700 may be compatible with more than one communication protocol. For example, the base station may be compatible with three protocols, such as a cellular telephone communication protocol, a two-way pager communication protocol, and BLUETOOTH® protocol. In such a case, a particular personal device 100 may be operable using a cellular telephone, a two-way pager, or a device compatible with BLUETOOTH®.

In one embodiment, the personal device 100 can communicate with a remote device using more than one communication protocols. For example, the personal device may include programming to determine which protocol to use for communicating.

The determination of which communication protocol to use to communicate with a remote device may be based on power requirements of each transceiver, based on the range to the remote device, based on a schedule, based on the most recent communication from the remote device, or based on any other measurable parameter. In one embodiment, the personal device 100 communicates simultaneously using multiple protocols.

In one embodiment, there are various types of networks connected to the base station 700. These may be telephone networks, modem connections, frame relay systems, spread-spectrum, DSL, cable modems, dedicated line or other similar wire based communication and data networks. In addition, these may be long-range, bi-directional, wireless networks as describe above.

In one embodiment, there is a connection to the Internet using various Internet protocols such as TCP/IP/HTTP/HTCP and others.

Other Connections from the Personal Medical Device

In one embodiment, signals generated by the medical device are received by a central monitoring station 800. The central monitoring station 800 may include operators that provide emergency dispatch services. An operator at the central monitoring station 800 may also attempt to verify the authenticity of a received alarm signal. In one embodiment, the alarm signal generated by the personal device 100 is first transmitted to a user, using either a short-range or long-range communication protocol, who then may forward the alarm signal to a monitoring station if authentic or cancel the alarm signal if the alarm is not valid.

In one embodiment, the personal device 100 may communicate with a building control or security system 900 by communicating using its transceiver. For example, the personal device may operate as an auxiliary input to a building control or security system. In which case, if the personal device 100 detects a security event, by way of a sensor coupled to the personal device, then an alarm signal is transmitted from the personal device, via its transceiver, to the building security system. The building security system, if monitored by a central monitoring station, then forwards the alarm signal to the monitoring station. In one embodiment, the personal device 100 can receive a transmission from a separate building control or security system. If the building security system detects an alarm condition, then the security system can, for example, instruct the personal device to repeatedly toggle power to load a flashing light visible from the exterior of the building that may aid emergency personnel in locating an emergency site. Alternatively, the personal device can establish communications with a predetermined remote device or a central monitoring service.

Routing Paths from the Personal Medical Device

The present invention includes, but is not limited to, the following routing paths from the personal device 100:

1 short-range wireless to long-range wireless in a pre-designed system. That is, both the personal device 100 and the device with which it communicates have been set up in communication in advance. For example, the personal device 100 is connected to a short-range wireless module that communicates to a cell phone or other wireless network device cared by the user.

2) short-range wireless to long-range wireless "ad hoc": the personal device sets up a short-range "ad hoc" network to any available long-range network connection.

3) short-range wireless to any network connection. For example, the personal device 100 is connected to a short-range wireless module that communicates to a telephone or Internet base station in a person's home.

4) long-range wireless directly. For example, the personal device 100 is directly connected to a long-range wireless network module.

Transmission to the Personal Medical Device

In addition, feedback may be transmitted to a remote device based on the operation of the personal device. For example, if a user issues a command to the personal device using a cellular telephone, then the display of the phone will indicate the changes arising from the command. In one embodiment, the cellular telephone, the base station, emergency monitoring center, or other device displays real time information from the personal device 100.

Various methods may be used to communicate with, or send a message or instruction to, the personal device 100 from a remote location. For example, using a cellular telephone, a user may speak a particular phrase, word or phoneme that is recognized by the cellular telephone which then generates and transmits a coded message to the personal device 100. As another example, the user may manipulate a keypad on the telephone to encode and transmit a message to the personal device.

Data Types Communicated to and from the Personal Medical Device

Table I below shows the types of data that may be communicated to and/or from the personal device 100, and the direction of data flow.

TABLE I

| Data Type | Direction of transmission |
|---|---|
| diagnosis (suggested by PMD/MDI or from medical center | bi-directional |
| manual request | from PMD |
| identification (e.g., bluetooth serial number, PMD ID, account number) | from PMD |
| use alert (e.g., opening a container, etc.) | from PMD |
| activation (shock, release medication, brain stimulation) | bi-directional |
| body reading (electrical, chemical, analog, digital, mechanical, temperature, etc.) | from PMD |
| two-way voice (to responding agency, bystander, or patient) | bi-directional |
| digital instructions | bi-directional |
| standard I/O ports | bi-directional |
| camera: visual, video exchange | bi-directional |
| authorizations and authentications | bi-directional |
| Security codes, data confirmations, acknowledgements | bi-directional |
| transceiver activation | to PMD |
| encryption | bi-directional |
| interaction with related PMDs | bi-directional |
| verification (alarms, emergencies) | bi-directional |

Data Flow Examples

Figure 5:
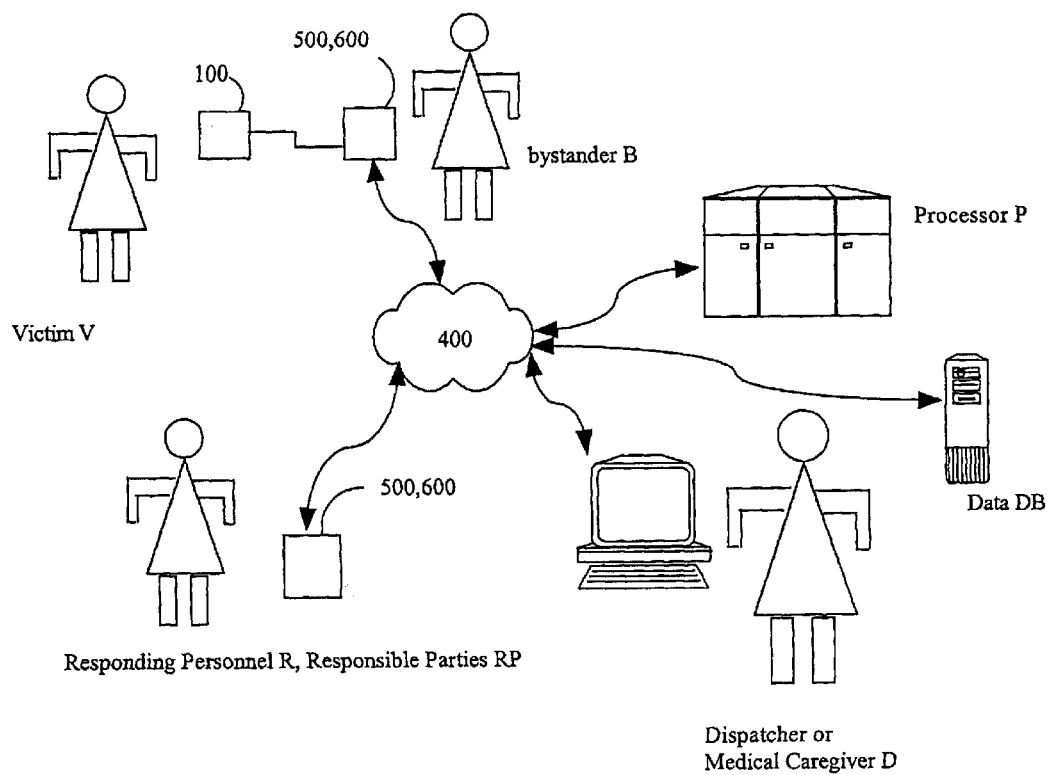
FIG. 5 is a network diagram showing communications through the system of the present invention.

One possible example of data flow to and from the personal device 100 is shown in FIG. 5.

The personal device 100 may be implanted in the victim V, or carried on the person of the victim V. For example the personal device 100 may be a pacemaker that is imbedded in the chest cavity of the victim V and connected by leads to the victim's heart, as is well known in the art.

In this example, the victim V undergoes some sort of cardiac problem, such as tachycardia, that causes the personal device 100 to attempt to establish communication with a caregiver. While this is going on, a bystander B attempts to give aid to the victim V. The bystander B is carrying on his person a medical device interface 500 or a personal wireless device 600. When the personal device 100 attempts to establish communication, it sets up communication with the personal wireless device 600 by local area wireless 330. For example, if the personal device 100 and personal wireless device 600 both use BLUETOOTH for local area wireless communications, the personal device 100 and personal wireless device 600 will follow the communications protocols of the BLUETOOTH standard and establish communications.

Next, the personal device 100 may request the personal wireless device 600 to establish a connection to the dispatcher or medical caregiver D, using network based communications 360. For example, the personal wireless device 600 may be a cell phone or PDA. Using network based communications 360, the personal wireless device establishes a connection to the computer of the dispatcher or medical caregiver D.

Alternatively, the personal wireless device 600 may establish a connection to an automatic processor P, which has database DB that contains information on the victim's medications, medical history, pre-existing conditions, possible diagnoses, personal records, personal device information, treatment strategies, response plans, identities or responsing agencies, and other data.

Either the dispatcher D or the processor P may then send an inquiry through the personal wireless device 600 to the personal device 100, instructing the personal device 100 to send various data, for example, electrocardiogram data. Using this transmitted data, the dispatcher or processor may then make a diagnosis and identify a treatment strategy.

The dispatcher D may then alert responding personnel R, such as a paramedic unit, to travel to the victim V. In the event that the victim's personal device 100 has location identification capability (discussed below), the dispatcher D will be able to give the exact location of the victim to the responding personnel R. The dispatcher D may also alert responsible parties RP such as the victim's parents of the location.

Until the responding personnel R reach the scene, the dispatcher D may establish voice communications with the bystander B through the bystander B's personal wireless device 600. The dispatcher may ask the bystander B to use the camera 280 of the personal wireless device to transmit an image of the victim V. The dispatcher D may give the bystander B instructions on how to render first aid to the victim V until the responding personnel R arrive.

When the responding personnel R reach the victim, they may establish communications through local area wireless 330 from their medical device interface 500 to the victim's personal device 100, request data from the personal device 100, and request the personal device 100 to take some action, such as dispensing medication to the victim V. Their medical device interface 500 may also establish communication with the dispatcher D or medical caregiver using network based communications 360.

The above is just one example of possible data flow to and from the personal device 100. Many other scenarios are possible.

Figure 6:
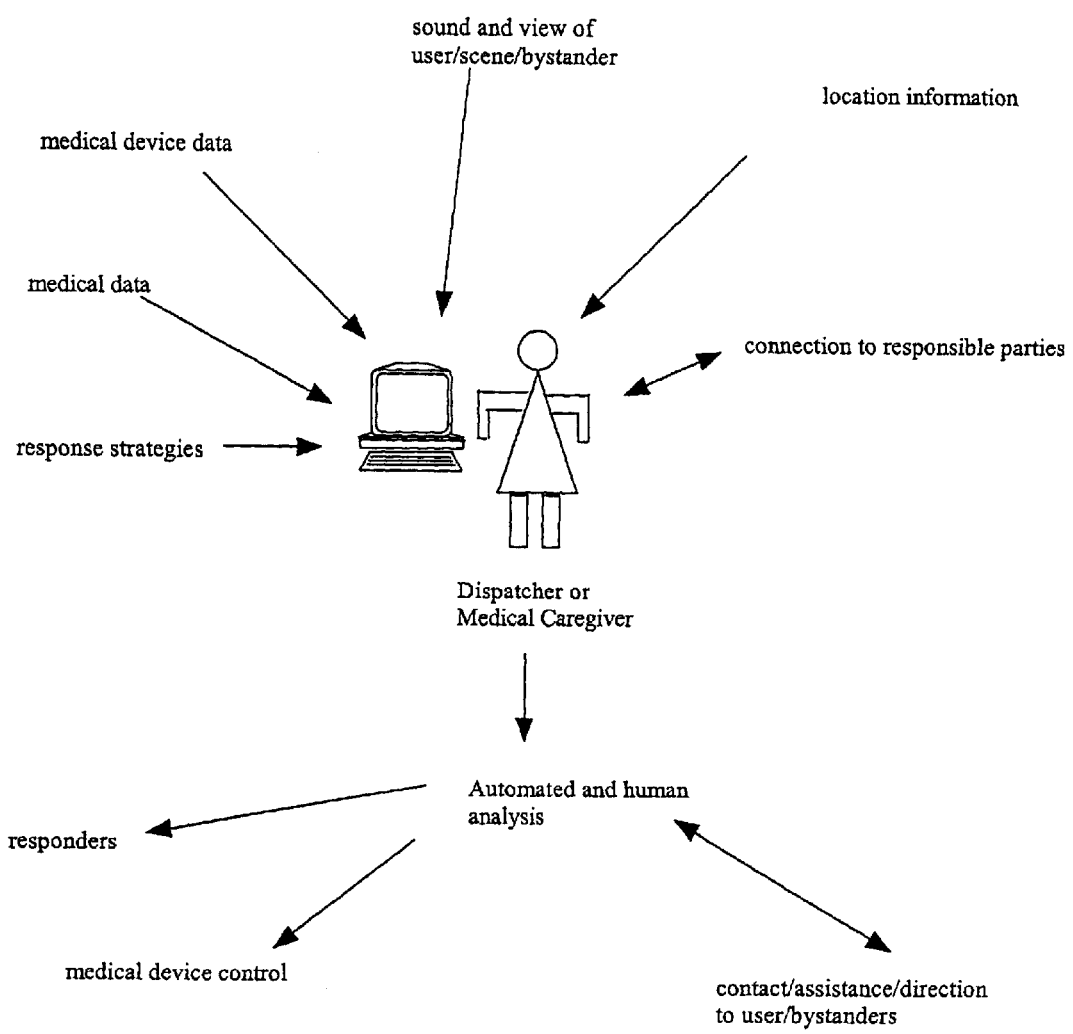
FIG. 6 is a chart showing the uses of various data by a dispatcher or medical caregiver.

FIG. 6 summarizes data flow from the point of view of a remote caregiver, showing that comprehensive data creates the best options for the remote caregiver.

Location Management

Optionally, the personal device 100 includes the ability to detect its own location and to communicate this location to authorized requesters. The location-determining function may be device-based, network-based, or a combination of device-based and network-based, as described in co-pending U.S. patent application entitled "Method and System for Wireless Tracking", filed Mar. 28, 2002, herein incorporated by reference, in the Detailed Description, and in FIGS. 4A, 4B and 4C therein.

As discussed in the referenced patent application (FIG. 4A), the personal device 100B may include a GPS receiver positioned internal to device 100*b*. FIG. 4B of the referenced patent illustrates a communication network 200A having integral LDS 165A. Location information, in one embodiment, is based on a geographical location of first device 100C and is determined based on timing information for wireless signals between network 200A and device 100C. Second device 300 is also connected to communication network 200A. In one embodiment, a server coupled to network 200A includes programming to determine location information and selected clients accessing the server are able to receive the location information. Selected clients are those authorized to receive the location information. FIG. 4C of the referenced patent application illustrates LDS 145B and LDS 165B within first device 100D and network 200B, respectively. In such an embodiment, the combination of information generated by LDS 145B and LDS 165B provides the location information.

As described in the referenced patent application, the device 100 may include an electronic circuit or an electronic circuit and programming to determine location. In one embodiment, LDS 145 uses a terrestrial location system. There are several varieties of terrestrial solutions, including time differential, signal strength, angle of arrival and varieties of triangulation. In one described embodiment, LDS 145 uses a combination of terrestrial and satellite navigation systems.

Security

The system and method of the present invention may also include various types of security arrangements.

It will be appreciated that the ability of various entities spread around a network to receive and/or transmit to and control the personal device 100 requires some measure of security. Only authorized agents should be allowed access to the device 100. For example, in the example shown in FIG. 5, only responding personnel RP (such as trained paramedics) who are on the scene of the event may be allowed to send a command to the personal device 100 causing the personal device 100 to dispense medication to the victim. Certainly, the bystander B should not be allowed this level of access, even though the bystander B's personal wireless device 600 may be acting as an intermediary in communication from the personal device 100 to the dispatcher D.

The following are possible embodiments of security and not meant to be exclusive.

First, data transmitted to and from the personal device 100 may be encrypted by standard encryption algorithms, making it essentially impossible for the unsophisticated interceptor to interpret the data.

Second, voice and visual channels of transmission may be controlled for activation by the personal device 100 or by an authorized entity, but may not necessarily be encrypted.

Third, security keys may be held by a central agency and provided to the responding personnel RP.

Fourth, the user of the personal device 100 may have a security key that he can enter to release information or access to authorized parties.

A number of strategies may be employed for authorization and authentication. For example, biometrics may be used. Biometrics refers to the measurement of some bodily parameter (such as fingerprint, retinal scan, etc.) that is unique to the individual.

Second, a public/private key system can be used in which access to both keys is required for decoding an encrypted message. Each party that wishes to participate in secure communications must create a key set for encrypting and decrypting messages. One key is private and the other is public. The public key is for exchanging with other parties with whom you who wish to participate in secure communication sessions. Each individual owner must keep the private portion of the key secure. The private key also has a secret pass phrase, in the event that it is ever 'misappropriated'. Public key/private key technology allows the sender to sign a message with their private key. When the recipient receives the message, they can validate the authenticity of the signature because they have the sender's public key.

Third, a user needing access to the device 100 may make a request for such access to a responsible third party.

Fourth, the personal device 100 may have pre-authorized authority for certain users.

A number of authorization strategies are discussed in co-pending U.S. patent Application, entitled "Method and System for Wireless Tracking", filed Mar. 28, 2002, herein incorporated by reference, in the Detailed Description.

About Power Management

In a number of scenarios, the power consumed by the personal device 100 is critical. For example, it the personal device 100 is implanted in a human being, long battery life is essential.

Although some communications systems, such as BLUETOOTH, have low power consumption states, nevertheless power is being consumed. Further, in an environment such as BLUETOOTH, a BLUETOOTH transceiver that is powered on may constantly be wakened from the low power states whenever a transmission is received from another BLUETOOTH transceiver.

It is therefore an important aspect of the present invention to provide a completely powered-off state for the bi-directional communications module, and for a means of signaling the bi-directional communications module to transition from the powered-off state to the powered-on state. The transceiver must consume no power in the powered-off state.

A number of mechanisms for doing this signaling are possible. First, a mechanical signal, such as throwing a switch or applying pressure to a pad, may be used. Second, a magnetic signal may be used, as in passing a magnet in the vicinity of the communications module. Third, sound or ultra-sound may be used. Fourth, infrared may be used provided there is a direct line of sight to the communications module. Sixth, radio frequency may be used, which has the advantage of not requiring line of sight to the communications module.

Radio frequency is already being used for applications such as automated meter reading and electronic article surveillance. Such applications included un-powered RF receivers such as RFID tags.

Figure 7:
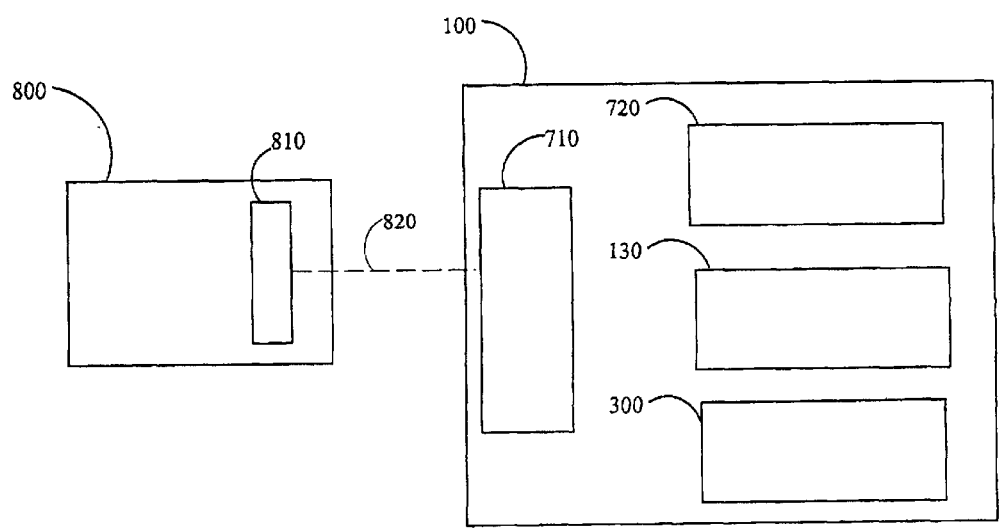
FIG. 7 is a block diagram of the power management function.

FIG. 7 shows a general block diagram of this power management function. The personal device 100 is modified to include an un-powered RF receiver 710 that is tuned to a particular frequency. Power-up device 800 has an RF transmitter tuned to the same frequency. When a signal is sent to the RF receiver 710, the receiver 710 gathers the RF energy and activates logic 720. Any code transmitted on the frequency is passed to the logic 720, which decodes it and compares it to a proper wake-up code. If a proper wake-up code is received, logic 720 signals the processor 130 to power-on the communications module 300. The wake-up code is optional, in that the receiver 710 may just signal the processor 130 directly without decode.

What is claimed:

1. A bi-directional wireless communication system comprising:
    (a) a first personal device, the first personal device further comprising:
        (i) a processor;
        (ii) a memory;

(iii) a power supply;
(iv) at least one detector input; and
(v) a short-range bi-directional wireless communications module;
(b) a second device communicating with the first device, the second device having a short-range bi-directional wireless communications module compatible with the short-range bi-directional wireless communications module of the first device; and
(c) a security mechanism governing information transmitted between the first personal device and the second device.

2. The system of claim 1, wherein the security mechanism encrypts the information.

3. The system of claim 1, wherein the security mechanism employs authorization by the first personal device.

4. The system of claim 1, wherein the security mechanism employs a key held by an agent and transmitted to the second device or wherein the security mechanism employs a key entered by a user of the first personal device.

5. The system of claim 1, wherein the security mechanism employs a private key and a public key.

6. The system of claim 1, wherein the security mechanism employs biometrics.

7. The system of claim 1, further comprising a detector connected to the at least one detector input.

8. The system of claim 7, wherein the detector senses body or physiological parameters.

9. The system of claim 8, wherein the body or physiological parameters are selected from the group consisting of temperature, motion, respiration, blood oxygen content, and electroencephalogram.

10. The system of claim 1, wherein the first personal device further comprises a user interface module.

11. The system of claim 10, wherein the user interface module further comprises a display, a data input means, and a speaker/microphone module.

12. The system of claim 10, wherein the user interface module further comprises a camera.

13. The system of claim 1, wherein the short-range wireless communications further comprises BLUETOOTH technology.

14. The system of claim 1, wherein the first personal device further comprises a data input/output port, the second device further comprises a data input/output port, and wherein the second device communicates with the first personal device using the data input/output ports.

15. The system of claim 1, further comprising a central communications base station communicating with the first personal device using short-range wireless communications.

16. The system of claim 15, wherein the short-range wireless communications is selected from the group consisting of HomeRF™, BLUETOOTH, and wireless LAN.

17. The system of claim 15, wherein the central communications base station further comprises long-range wireless communications.

18. The system of claim 17, wherein the long-range wireless communications is selected from the group consisting of cellular, satellite, paging, narrowband PCS, and narrowband trunk radio.

19. The system of claim 18, further comprising long-range messaging protocols executing over the long-range wireless communications.

20. The system of claim 19, wherein the long-range messaging protocols are selected from the group consisting of wireless application protocol, cellular telephone protocols, one-way pager protocols, two-way pager protocols, and PCS protocols.

21. The system of claim 15, wherein the central communications base station further comprises an interface to a long-distance telephone network.

22. The system of claim 15, wherein the central communications base station further comprises a connection to the Internet.

23. The system of claim 1, further comprising a central monitoring station receiving alarm signals from the first personal device.

24. The system of claim 1, wherein the first personal device further comprises a location determination module that determines the geographical location of the first personal device.

25. The system of claim 24, wherein the location determination module further comprises a GPS receiver.

26. The system of claim 1, wherein the bi-directional communications module has a powered-down state and a powered-up state, and further comprising a means for signaling the bi-directional communications module to transition from the powered-down state to the powered-up state.

27. The system of claim 26, wherein the means for signaling is mechanical.

28. The system of claim 26, wherein the means for signaling is magnetic.

29. The system of claim 26, wherein the means for signaling is sound or ultra-sound.

30. The system of claim 26, wherein the means for signaling is infrared.

31. The system of claim 26, wherein the means for signaling is radio frequency.

32. The system of claim 1, wherein the first personal device is implantable in a person.

33. A bi-directional wireless communication system comprising:
(a) a first personal device, the first personal device further comprising:
(i) a processor;
(ii) a memory;
(iii) a power supply;
(iv) at least one detector input; and
(v) a long-range bi-directional wireless communications module;
(b) a long-range bi-directional wireless network communicating with the long-range bi-directional wireless communications module;
(c) an entity communicating with the first personal device over the network; and
(d) a security mechanism governing information transmitted between the first personal device and the entity.

34. The system of claim 33, wherein the long-range wireless communications network is selected from the group consisting of cellular, satellite, paging, narrowband PCS, and narrowband trunk radio.

35. The system of claim 34, further comprising long-range messaging protocols executing over the long-range wireless communications network.

36. The system of claim 35, wherein the long-range messaging protocols are selected from the group consisting of wireless application protocol, cellular telephone protocols, one-way pager protocols, two-way pager protocols, and PCS protocols.

37. The system of claim 33, wherein the first personal device further comprises a location determination module that determines the geographical location of the first personal device.

38. The system of claim 37, wherein the location determination module further comprises a GPS receiver.

39. The system of claim 33, wherein the bi-directional communications module has a powered-down state and a powered-up state, and further comprising a means for signaling the bi-directional communications module to transition from the powered-down state to the powered-up state.

40. The system of claim 39, wherein the means for signaling is selected from the group consisting of mechanical, magnetic, sound or ultrasound, infrared, and radio frequency.

41. The system of claim 39, wherein the security mechanism encrypts the information.

42. The system of claim 33, wherein the security mechanism employs authorization by the first personal device.

43. The system of claim 33, wherein the security mechanism employs a key held by an agent and transmitted to the second device.

44. The system of claim 33, wherein the security mechanism employs a key entered by a user of the first personal device.

45. The system of claim 33, wherein the security mechanism employs a private key and a public key.

46. The system of claim 33, wherein the security mechanism employs biometrics.

47. The system of claim 33, wherein the first personal device is implantable in a person.

48. A bi-directional wireless communication system comprising:
- (a) a first personal device, the first personal device further comprising:
  - (i) a processor;
  - (ii) a memory;
  - (iii) a power supply;
  - (iv) at least one detector input; and
  - (v) a short-range bi-directional wireless communications module;
- (b) a second device communicating with the first personal device, the second device having a short-range bi-directional wireless communications module compatible with the short-range bi-directional wireless communications module of the first personal device and also having a long-range bi-directional wireless communications module; and
- (c) a long-range bi-directional wireless network communicating with the long-range bi-directional wireless communications module of the second device.

49. The system of claim 48, wherein the short-range wireless communications further comprises BLUETOOTH technology.

50. The system of claim 48, wherein the long-range wireless communications network is selected from the group consisting of cellular, satellite, paging, narrowband PCS, and narrowband trunk radio.

51. The system of claim 50, further comprising long-range messaging protocols executing over the long-range wireless communications network.

52. The system of claim 51, wherein the long-range messaging protocols are selected from the group consisting of wireless application protocol, cellular telephone protocols, one-way pager protocols, two-way pager protocols, and PCS protocols.

53. The system of claim 48, wherein the bi-directional wireless communications module of the first personal device has a powered-down state and a powered-up state, and further comprising a means for signaling the bi-directional wireless communications module of the first personal device to transition from the powered-down state to the powered-up state.

54. The system of claim 53, wherein the means for signaling is selected from the group consisting of mechanical, magnetic, sound or ultrasound, infrared, and radio frequency.

55. A method of bi-directional communications, comprising the steps of:
- (a) detecting an event by a detector connected to a first personal device;
- (b) signaling the event to a second device using short-range bi-directional wireless communications between the first personal device and the second device;
- (c) wherein the short-range wireless communications is BLUETOOTH; and
- (d) wherein a security mechanism controls recognition of the event by the second device.

56. The method of claim 55, further comprising the step of transitioning the first personal device from a powered-down state to a powered-up state by means of an external radio frequency stimulus.

57. The method of claim 56, further comprising the step of signaling the event from the second device to a long-range bi-directional network.

\* \* \* \* \*

(12) INTER PARTES REVIEW CERTIFICATE (3289th)

United States Patent
Menard

(10) Number: US 7,088,233 K1
(45) Certificate Issued: Oct. 26, 2023

(54) PERSONAL MEDICAL DEVICE COMMUNICATION SYSTEM AND METHOD

(75) Inventor: Raymond J. Menard

(73) Assignee: PHILIPS NORTH AMERICA LLC

Trial Numbers:

IPR2020-00783 filed Apr. 8, 2020
IPR2020-00910 filed May 15, 2020

Inter Partes Review Certificate for:

Patent No.: 7,088,233
Issued: Aug. 8, 2006
Appl. No.: 10/165,624
Filed: Jun. 7, 2002

The results of IPR2020-00783 joined with IPR2020-00910 are reflected in this inter partes review certificate under 35 U.S.C. 318(b).

INTER PARTES REVIEW CERTIFICATE
U.S. Patent 7,088,233 K1
Trial No. IPR2020-00783
Certificate Issued Oct. 26, 2023

AS A RESULT OF THE INTER PARTES REVIEW PROCEEDING, IT HAS BEEN DETERMINED THAT:

Claim 14 is found patentable.

Claims 1, 7-10, 13, 15, 16, 22 and 24-26 are cancelled.

\* \* \* \* \*